United States Patent
Salsman et al.

(10) Patent No.: US 8,538,120 B2
(45) Date of Patent: Sep. 17, 2013

(54) SYSTEM FOR TARGETING CELLS OR OTHER MATERIALS

(75) Inventors: Kenneth Edward Salsman, Pleasanton, CA (US); Ulrich Boettiger, Boise, ID (US); Dmitry Bakin, San Jose, CA (US); Curtis W. Stith, Santa Cruz, CA (US)

(73) Assignee: Aptina Imaging Corporation, George Town (KY)

( * ) Notice: Subject to any disclaimer, the term of this patent is extended or adjusted under 35 U.S.C. 154(b) by 245 days.

(21) Appl. No.: 13/114,982

(22) Filed: May 24, 2011

(65) Prior Publication Data
US 2012/0045103 A1    Feb. 23, 2012

Related U.S. Application Data

(60) Provisional application No. 61/439,326, filed on Feb. 3, 2011, provisional application No. 61/375,227, filed on Aug. 19, 2010.

(51) Int. Cl.
*G06K 9/00* (2006.01)

(52) U.S. Cl.
USPC ............................. 382/133; 348/79; 378/43

(58) Field of Classification Search
USPC ............. 382/100, 128, 129, 130, 131, 133, 382/134; 850/6, 9, 14; 378/43, 47; 250/309
See application file for complete search history.

(56) References Cited

U.S. PATENT DOCUMENTS

| | | | |
|---|---|---|---|
| 6,456,754 B1 * | 9/2002 | Augustsson | 385/24 |
| 7,391,053 B2 * | 6/2008 | Iizuka et al. | 257/59 |
| 7,452,726 B2 * | 11/2008 | Chou et al. | 436/63 |
| 7,492,167 B2 * | 2/2009 | Reich et al. | 324/663 |
| 7,695,683 B2 * | 4/2010 | Quan et al. | 422/504 |
| 7,773,227 B2 * | 8/2010 | Yang et al. | 356/436 |
| 7,863,035 B2 * | 1/2011 | Clemens et al. | 435/287.1 |
| 7,868,665 B2 * | 1/2011 | Turner et al. | 327/70 |
| 8,325,349 B2 * | 12/2012 | Cui et al. | 356/515 |
| 2010/0054574 A1 * | 3/2010 | Marcelpoil et al. | 382/133 |
| 2012/0250027 A1 * | 10/2012 | Zheng et al. | 356/491 |

OTHER PUBLICATIONS

Cui et al., "Lensless high-resolution on-chip optofluidic microscopes for *Caenorhabditis elegans* and cell imaging" [online], May 2008 [retrieved on May 11, 2011]. Retrieved from the Internet: http://www.biophot.caltech.edu/publications/pdf/2008-OFM-PNAS.pdf.

(Continued)

*Primary Examiner* — Anand Bhatnagar
(74) *Attorney, Agent, or Firm* — Treyz Law Group; Louis R. Levenson (57) ABSTRACT

An image sensor integrated circuit may contain image sensor pixels. A channel containing a fluid with particles such as cells may be formed on top of the image sensor. Some of the image sensor pixels may form a calibration sensor and some of the image sensor pixels may form an imager. As the fluid and particles flow through the channel at a flow rate, the calibration sensor may measures the flow rate and illumination intensity in the channel. Based on calibration data such as measured flow rate and measured illumination intensity, adjustments may be made to ensure that the imager acquires satisfactory image data. The adjustments may include flow rate adjustments, image acquisition data rate adjustments, and illumination adjustments. A processing unit in the channel may contain a laser or other component to destroy selected cells. A flared region in the channel may be used as a chromatograph.

11 Claims, 7 Drawing Sheets

(56) References Cited

OTHER PUBLICATIONS

Cui et al., "Quantitative differential interference contrast microscopy based on structured-aperture interference" [online], Sep. 2008 [retrieved on May 11, 2011]. Retrieved from the Internet: http://www.biophot.caltech.edu/publications/pdf/Cui-APL-2007-DIC.pdf.

Wu et al., "The application of Fresnel zone plate based projection in optofluidic microscopy" [online], Sep. 2008 [retrieved on May 11, 2011]. Retrieved from the Internet: http://www.biophot.caltech.edu/publications/pdf/Wu-OE-2008-Fresnel.pdf.

Stith et al., U.S. Appl. No. 13/205,340, filed Aug. 8, 2011.
Stith et al., U.S. Appl. No. 13/114,980, filed May 24, 2011.
Stith et al., U.S. Appl. No. 13/114,990, filed May 24, 2011.

* cited by examiner

SYSTEM FOR TARGETING CELLS OR OTHER MATERIALS

This application claims the benefit of provisional patent application No. 61/439,326, filed Feb. 3, 2011, and provisional patent No. 61/375,227, filed Aug. 19, 2010, which are hereby incorporated by reference herein in their entireties.

BACKGROUND

This relates generally to systems such as optofluidic microscope systems, and, more particularly, to using such systems to image and process cells and other specimens.

Optofluidic microscopes have been developed that can be used to generate images of cells and other biological specimens. The cells are suspended in a fluid. The fluid flows over a set of image sensor pixels in a channel. The image sensor pixels may be associated with an image sensor pixel array that is masked using a metal layer with a pattern of small holes. In a typical arrangement, the holes and corresponding image sensor pixels are arranged in a diagonal line that crosses the channel. As cells flow through the channel, image data from the pixels may be acquired and processed to form high-resolution images of the cells.

DETAILED DESCRIPTION

Figure 1:
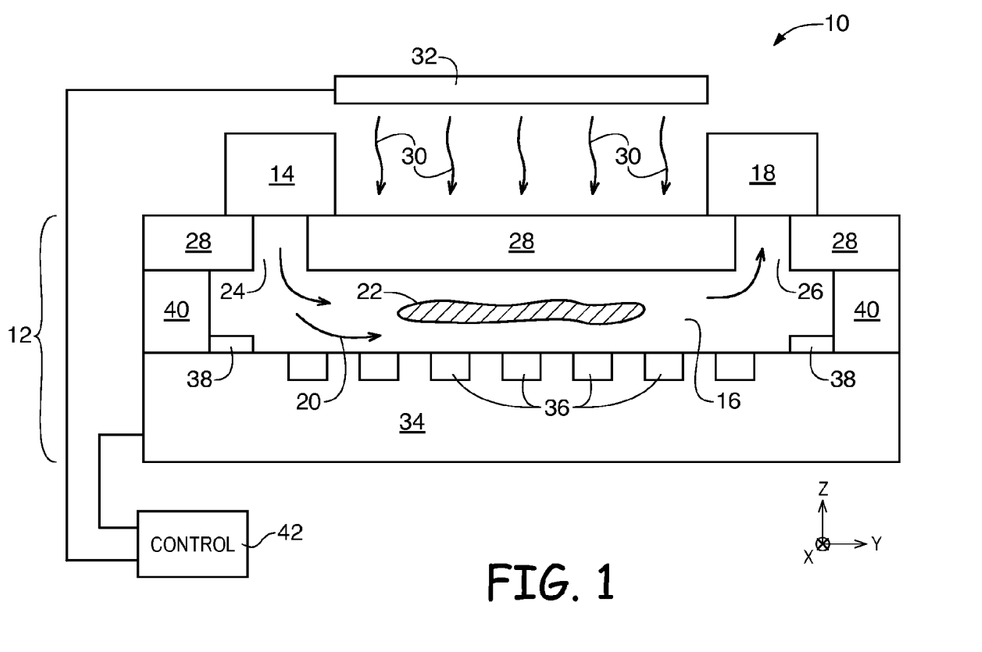
FIG. 1 is a diagram of an illustrative system for imaging and processing cells and other biological specimens in accordance with an embodiment of the present invention.

A system of the type that may be used to image and process cells and other samples such as biological specimens is shown in FIG. 1. As shown in FIG. 1, system 10 may include optofluidic microscope 12. Microscope 12 may include an image sensor integrated circuit such as image sensor integrated circuit 34. Image sensor integrated circuit 34 may be formed from a semiconductor substrate material such as silicon and may contain numerous image sensor pixels 36. Image sensor pixels 36 may form part of an array of image sensor pixels on image sensor integrated circuit 34. Some of the pixels may be actively used for gathering light. Other pixels may be inactive or may be omitted from the array during fabrication. In arrays in which fabricated pixels are to remain inactive, the inactive pixels may be covered with metal or other opaque materials, may be depowered, or may otherwise be inactivated. There may be any suitable number of pixels fabricated in integrated circuit 34 (e.g., tens, hundreds, thousands, millions, etc.). The number of active pixels in integrated circuit 34 may be tens, hundreds, thousands, or more).

Image sensor integrated circuit 34 may be covered with a transparent layer of material such as glass layer 28 or other clear covering layers. Structures such as standoffs 40 (e.g., polymer standoffs) may be used to elevate the lower surface of glass layer 28 from the upper surface of image sensor integrated circuit 34. This forms one or more channels such as channels 16. Channels 16 may have lateral dimensions (dimensions parallel to dimensions x and z in the example of FIG. 1) of a millimeter or less (as an example). The length of each channel (the dimension of channel 16 along dimension y in the example of FIG. 1) may be 1-10 mm, less than 10 mm, more than 10 mm, or other suitable length. Standoff structures 40 may be patterned to form sidewalls for channels such as channel 16.

During operation, fluid flows through channel 16 as illustrated by arrows 20. A fluid source such as source 14 may be used to introduce fluid into channel 16 through entrance port 24. Fluid may, for example, be dispensed from a pipette, from a drop on top of port 24, from a fluid-filled reservoir, from tubing that is coupled to an external pump, etc. Fluid may exit channel 16 through exit port 26 and may, if desired, be collected in reservoir 18. Reservoirs may also be formed within portions of channel 16.

The rate at which fluid flows through channel 16 may be controlled using fluid flow rate control structures. Examples of fluid flow rate control structures that may be used in system 10 include pumps, electrodes, microelectromechanical systems (MEMS) devices, etc. As shown in FIG. 1, for example, channel 16 may be provided with electrodes such as electrodes 38. By controlling the voltage applied across electrodes such as electrodes 38, the flow rate of fluids in channel 16 such as ionic fluids may be controlled by control circuitry 42.

Fluid 20 may contain cells such as cell 22 or other biological elements or particles. As cells such as cells 22 pass by sensor pixels 36, image data may be acquired. In effect, the cell is "scanned" across the pattern of sensor pixels 36 in channel 16 in much the same way that a printed image is scanned in a fax machine. Control circuitry 42 (which may be implemented as external circuitry or as circuitry that is embedded within image sensor integrated circuit 34) may be used to process the image data that is acquired using sensor pixels 36. Because the size of each image sensor pixel 36 is typically small (e.g., on the order of 0.5-3 microns or less in width), precise image data may be acquired. This allows high-resolution images of cells such as cell 22 to be produced. A typical cell may have dimensions on the order of 1-10 microns (as an example). Images of other samples (e.g., other biological specimens) may also be acquired in this way.

Arrangements in which cells are imaged are sometimes described herein as an example.

During imaging operations, control circuit 42 (e.g., on-chip and/or off-chip control circuitry) may be used to control the operation of light source 32. Light source 32 may be based on one or more lamps, light-emitting diodes, lasers, or other sources of light. Light source 32 may be a white light source or may contain one or more light-generating elements that emit different colors of light. For example, light-source 32 may contain multiple light-emitting diodes of different colors or may contain white-light light-emitting diodes or other white light sources that are provided with different respective colored filters. In response to control signals from control circuitry 42, light source 32 may produce light 30 of a desired color and intensity. Light 30 may pass through glass layer 28 to illuminate the sample in channel 16.

Figure 2:
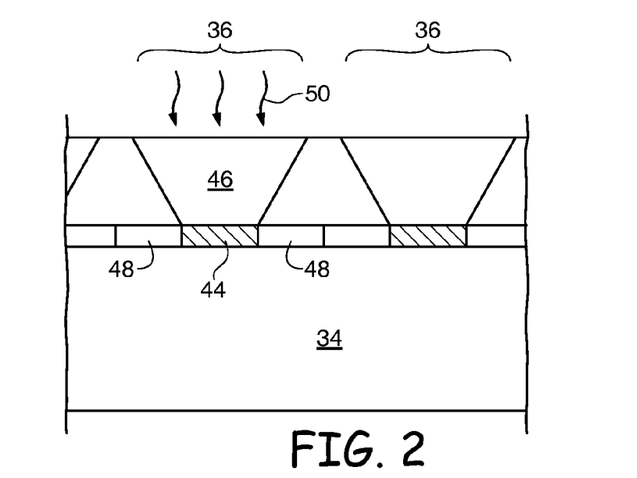
FIG. 2 is a cross-sectional side view of a portion of an image sensor pixel array of the type that may be used in a fluid channel in a system of the type shown in FIG. 1 in accordance with an embodiment of the present invention.

A cross-sectional side view of illustrative image sensor pixels 36 is shown in FIG. 2. As shown in FIG. 2, image sensor pixels 36 on integrated circuit 34 may each include a corresponding photosensitive element such as photodiode 44. Light guides such as light guide 46 may be used to concentrate incoming image light 50 into respective photodiodes 44. Photodiodes 44 may each convert incoming light into corresponding electrical charge. Circuitry 48, which may form part of control circuitry 42 of FIG. 1, may be used to convert the charge from photodiodes 44 into analog and/or digital image data. In a typical arrangement, data is acquired in frames. Control circuitry 42 may convert raw digital data from one or more acquired image data frames into images of cells 22.

To ensure that image data is captured accurately, it may be desirable to make adjustments to system 10 such as adjustments to the intensity of light 30 that is produced by light source 32, adjustments to the flow rate of fluid 20 and cells 22, and adjustments to the image acquisition data rate used in gathering image data from image sensor pixels 36 (e.g., the frame rate). Adjustments to the intensity of light 30 and the image acquisition settings for pixels 36 may, for example, be used to ensure that data is properly exposed. If too much light is present during an acquired frame of data, photodiodes 44 may saturate. If insufficient light is present, the data may be noisy. Flow rate adjustments affect the resolution of acquired images. If, for example, the flow rate of fluid 20 in channel 16 is too high, insufficient data will be acquired by image sensors 36 and the resulting resolution of the images of cells 22 may be poor.

Figure 3:
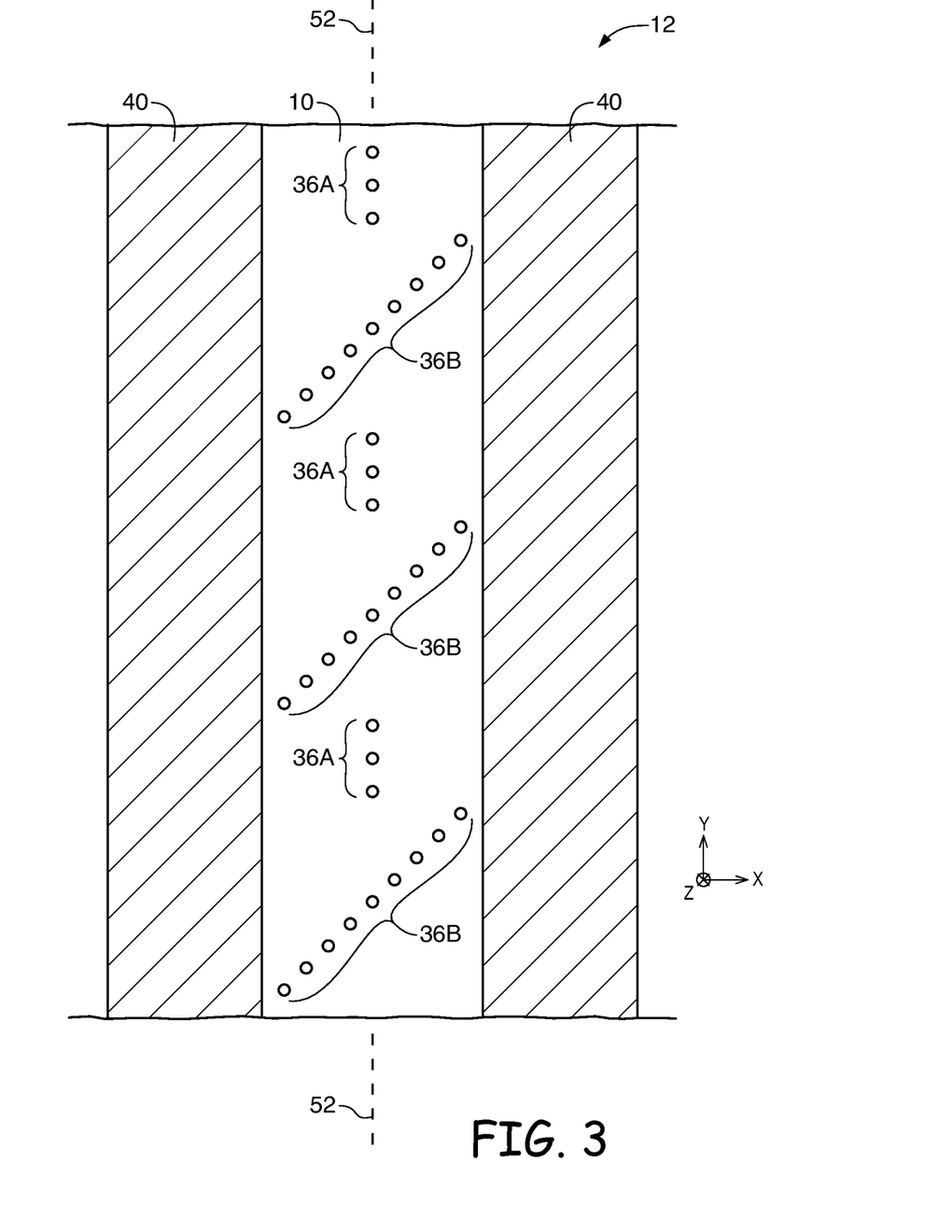
FIG. 3 is a top view of an illustrative fluid channel having calibration pixels and imaging pixels in accordance with an embodiment of the present invention.

As shown in FIG. 3, channel 16 may be provided with calibration pixels such as image sensor pixels 36A and imaging pixels such as image sensor pixels 36B. Pixels 36A and 36B may be formed using structures of the type shown by image sensor pixels 36 of FIG. 2 (as an example). One or more sets of calibration pixels 36A may be alternated with one or more corresponding sets of imaging pixels 36B along the length of channel 16. In the FIG. 3 example, there are three sets of calibration pixels 36A and three corresponding sets of imaging pixels 36B. This is merely illustrative. There may be, for example, only a single set of calibration pixels 36A and a single corresponding set of imager pixels 36B, there may be two sets of calibration pixels 36A and two corresponding sets of imager pixels 36B, or there may be three or more sets of calibration pixels 36A and imager pixels 36B. Arrangements in which there are different numbers of sets of calibration pixels and imager pixels may also be used.

Each set of calibration pixels 36A preferably includes at least some image sensor pixels that are arranged parallel to the longitudinal dimension of channel 16 (axis 52) so that the calibration pixels may be used to gather movement data from intensity fluctuations arising from the movement of cells over the calibration pixels (e.g., data on the flow rate of fluid 20 and cells 22). There may be any suitable number of pixels 36A in each set of calibration pixels (e.g., one, two, three, more than three, etc.). Calibration pixels 36A may be arranged in a vertical row (parallel to longitudinal axis 52 and dimension Y in the FIG. 3 example), or in other suitable shapes. The sets of calibration pixels 36A are sometimes referred to as forming calibration regions or calibration sensors. The calibration sensors may serve as flow sensors and/or as light sensors (e.g., light meters for evaluating light illumination levels in channel 16). For example, by measuring the amount of time between successive light intensity fluctuations in the calibration pixels 36A due to a cell that is passing successively over each of the calibration pixels 36A, the speed of the cell and therefore the flow rate of the fluid in which the cell is being carried can be computed. Based on data from each calibration sensor, control circuitry 42 may adjust settings in system 10 to ensure that image data is satisfactorily gathered in an associated set of image acquisition pixels 36B (i.e., an associated imager). Each set of image acquisition pixels may form a diagonal region or other region of image acquisition pixels in channel 16. The use of a diagonal set of image acquisition pixels 36B in channel 16 may help improve resolution (i.e., lateral resolution in dimension x perpendicular to longitudinal axis 52), by increasing the number of pixels 36B per unit length in dimension x. The sets of image acquisition pixels 36B in channel 16 are sometimes referred to as image acquisition regions, image sensors, or imagers.

In some situations, it may be desirable to gather image data in different portions of the light spectrum. Light source 32 may be adjusted to produce different colors of light during image acquisition operations. The different colors of light may be used in gathering image data in different color channels. A different light color may be used in illuminating cells 22 as cells 22 pass respective imagers in channel 16.

For example, it may be desirable to separately image cells 22 using red, blue, and green light. With an arrangement of the type shown in FIG. 3, each calibration sensor (i.e., each set of pixels 36A in a respective calibration region) and associated imager (i.e., each set of pixels 36B in a respective image acquisition region) may be used in gathering image data for a different color channel as fluid 20 flows through channel 16. The calibration sensors may be used in determining appropriate settings for capturing satisfactory images. The imagers may be used in gathering corresponding image data. With one suitable arrangement, which is sometimes described herein as an example, the uppermost calibration sensor and imager in channel 16 may be used in gathering red channel data while illumination light 30 is red, the middle calibration sensor and the middle imager in channel 16 may be used in gathering blue channel data while illumination light 30 is blue, and the lowermost calibration sensor and imager in channel 16 may be used in gathering green channel data while illumination light 30 is green. Other arrangements are possible in which one or more pixels from of each set of pixels 36A or 36B may be used in gathering infrared channel data, in gathering ultraviolet channel data, or in gathering data using light having a specific range of wavelengths (e.g. 530 nm-540 nm light), or in gathering a combination of color channel data.

Figure 4:
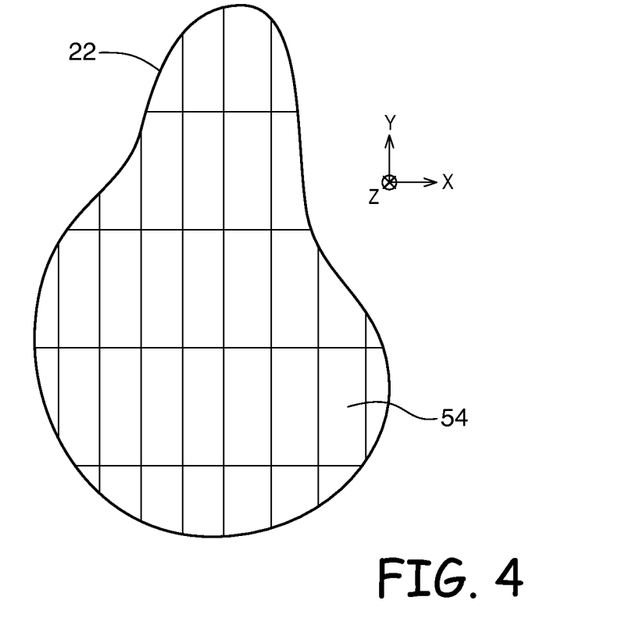
FIG. 4 is a diagram showing how image pixel data may correspond to elongated regions on a specimen when image acquisition and flow rate settings are not adjusted optimally in accordance with an embodiment of the present invention.
Figure 5:
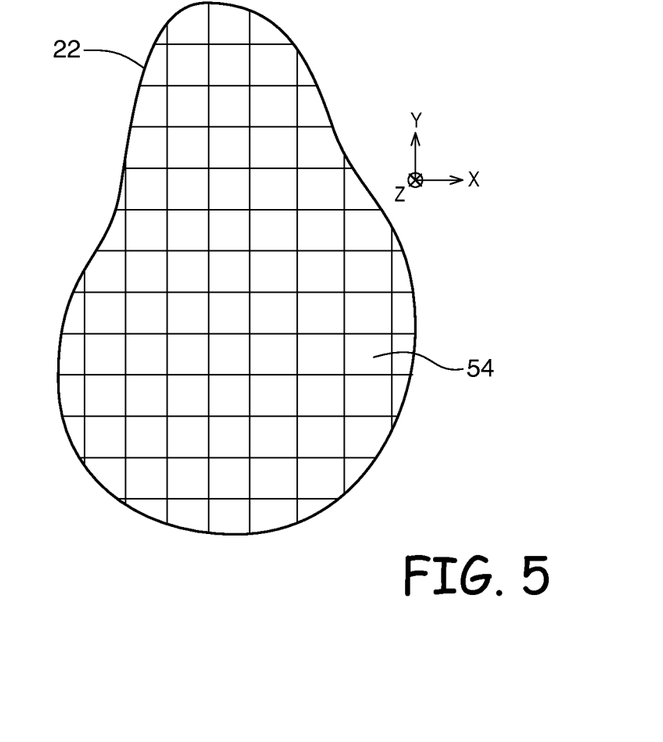
FIG. 5 is a diagram showing how image pixel data may be associated with regions of a specimen having equally sized horizontal and vertical components when image acquisition and flow rate settings are adjusted optimally in accordance with an embodiment of the present invention.

As cells pass each calibration sensor, the calibration sensor may be used to measure the flow rate for the cells and may be used to make a light measurement. The flow rate and light measurement may be used in adjusting the settings for system 10. For example, if the amount of measured light is low, the exposure time used for the imager may be increased and the frame rate of the acquired data may, if desired, be lowered. As another example, consider the impact of flow rate on the image acquisition process. For a given frame rate, it is generally desirable to adjust the flow rate to ensure that the vertical and horizontal resolutions of the acquired images are comparable. If the flow rate is too high, each image sensor pixel 36B in a given imager will acquire image data that is smeared out over a relatively elongated region. As shown in FIG. 4, this may result in pixel data regions 54 that are elongated in dimension Y relative to dimension X, as shown in FIG. 4. More optimally, the flow rate for fluid 20 and cells 22 is adjusted so that each acquired image pixel data value 54 corresponds to a region of cell 22 with comparable x and y dimensions as shown in FIG. 5. Balancing the resolution of the images in this way helps ensure that the acquired images exhibit good quality without overwhelming buffer circuits and other image processing circuits in circuitry 42 with excess data. In general, fluid flow rate and/or the rate of image acquisition (e.g., the frame rate of each imager) may be adjusted.

Figure 6:
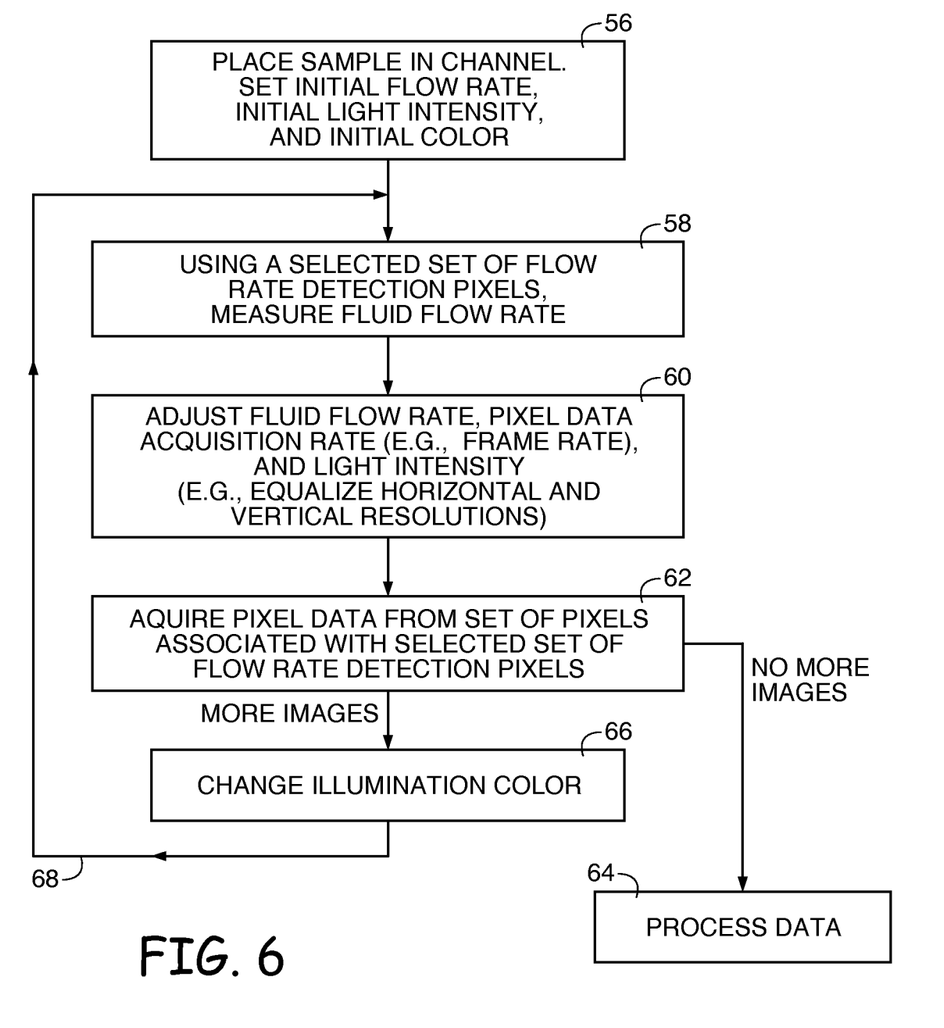
FIG. 6 is a flow chart of illustrative steps involved in acquiring images using a system of the type shown in FIG. 1 in accordance with an embodiment of the present invention.

FIG. 6 is a flow chart of illustrative steps involved in using a system such as system 10 of FIG. 1 having calibration sensors and imagers of the type shown in FIG. 3 in acquiring images of cells 22 or other samples. At step 56, a user of system 10 may place a sample in system 10. In particular, a sample such as a fluid sample containing cells or other biological specimens may be placed at the upper end of channel 16 of FIG. 3. Electrodes 38 or other fluid flow control mechanism may be used to cause the fluid sample to flow through channel 16 over calibration sensors and imagers. During the setup operations of step 56, light source 32 may be adjusted to produce an initial amount of illumination of an initial color (e.g., red).

After setting the illumination color, the cells 22 in the fluid of the sample may flow over the set of image sensor pixels 36A in the first calibration sensor (e.g., the uppermost set of three calibration image sensor pixels 36A of FIG. 3) for calibration (step 58). During the calibration operations of step 58, the pixels in the calibration sensor may be used to measure the flow rate. The collective amount of light 30 reaching the pixels in the calibration sensor may be used to produce a light intensity reading.

Based on the measured amount of light and the measured flow rate from step 58, at step 60, the fluid flow rate, the image acquisition rate for the corresponding imager (i.e., the frame rate for use by pixels 36B in the uppermost set of image sensor pixels in FIG. 3), the light intensity from source 32 (i.e., the amount of red light from source 32), and other suitable parameters may be adjusted to ensure that acquired images will have satisfactory quality (i.e., to ensure that images will be properly exposed, to ensure that horizontal and vertical resolutions are balanced as described in connection with FIGS. 5 and 6, etc.).

At step 62, the imager that is associated with the first calibration sensor may be used to acquire images of the sample. If all desired image data has been collected, processing may proceed to step 64, where final image processing operations may be completed. For example, the operations of step 64 may be used to combine image data from multiple color channels, may be used to stitch together data from multiple data frames, and may otherwise be used in processing the data from the imagers to form completed images of the cells or other particles in the fluid.

If more data is to be acquired (e.g., for additional color channels such as blue and green color channels), the color of light 30 that is produced by light source 32 may be updated (e.g., from red to blue or from blue to green, as appropriate) during step 66. As the cells pass additional calibration sensors and additional corresponding imagers, additional data may be acquired (i.e., processing may loop back to step 58, as indicated by line 68). Once data for all desired colors has been obtained, processing may proceed to step 64.

For example, in a system of the type shown in FIG. 3 in which there are three calibration sensors and three corresponding imagers, the first (uppermost) calibration sensor may be used in determining the flow rate of the cells and the light reading for the cells when illuminated by red light and these settings may be used in acquiring red image data using the first (uppermost) imager while source 32 is producing red light. The cells may then flow over the second (middle) calibration sensor while the light source produces blue illumination. The second calibration sensor may be used in determining the flow rate of the cells and the light reading for the cells when illuminated by blue light and these settings may be used in acquiring blue image data using the second (middle) imager while source 32 is producing blue light. Following acquisition of blue light data, the cells may flow over the third (lowermost) calibration sensor while the light source produces green illumination. The third calibration sensor may be used in determining the flow rate of the cells and the light reading for the cells when illuminated by green light and these settings may be used in acquiring green image data using the third (lowermost) imager while source 32 is producing green light. During the operations of step 64, the image data from the red, blue, and green channels may be combined to form a color image of cells 22.

If desired, additional colors of illumination or different colors of illumination may be used. The use of red, blue, and green as illumination colors is merely an example. Moreover, it is not necessary for channel 16 to contain multiple imagers and calibration sensors. A single calibration sensor may be shared among multiple imagers if desired. The flow of fluid 20 may be reversed so that cells 22 pass over a given imager (and, if desired, a given calibration sensor) multiple times. During each pass, cells 22 may be imaged using a different color of light 30.

Images of cells 22 and other biological specimens may be used to identify diseased cells or other cells for which additional processing may be desired. For example, the images of cells 22 that are acquired using the imagers of FIG. 3 may be used to identify cells that should be destroyed by application of heat or laser light (as examples). The images of cells 22 may also be used in identifying parts of cells 22 to which heat or laser light should be applied. In some situations, additional diagnostic processing may be desired. For example, it may be desirable to perform density measurements, fluorescence measurements, or spectroscopic measurements on cells 22 after cells 22 have been imaged. In a fluorescence measurement, for example, a dye in cells 22 may be illuminated with a laser or one or more additional light sources. This may cause a particular portion of cell 22 to fluoresce. Using the acquired images of cells 22, the location within each cell 22 that is fluorescing may be identified. In spectroscopic measurements, light of a variety of wavelengths may be applied to the cells (e.g., to gather transmission spectra, reflection spectra, fluorescent spectra, etc.).

Figure 7:
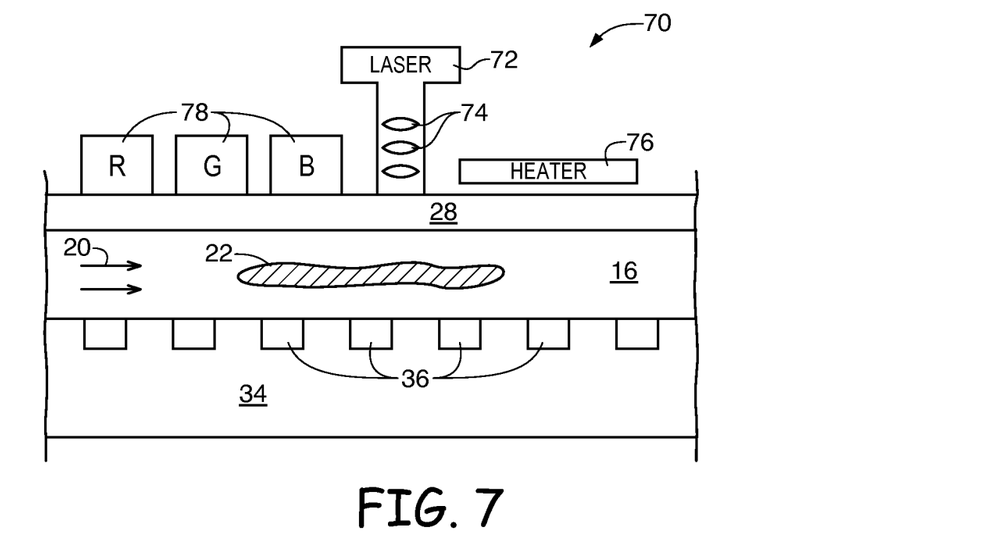
FIG. 7 is a cross-sectional diagram of illustrative sample processing structures that may be used in an imaging and processing system of the type shown in FIG. 1 in accordance with an embodiment of the present invention.

Illustrative structures that may be used in post-processing cells 22 following imaging are shown in FIG. 7. As shown in FIG. 7, processing unit 70 may include one or more cell processing (sample processing) components such as laser 72, light sources 78, and heater 76. Processing unit 70 may also include light sensors such as image sensor pixels 34 on image sensor integrated circuit 34. Laser 72 may include a laser source such as a semiconductor laser and associated optics (e.g., lenses 74). Light sources 78 may be based on one or more light-emitting diodes, one or more lamps, color filters to provide the light-emitting diodes and/or lamps with desired colors, or other sources of light. Heater 76 may be a resistive (ohmic) heater (as an example). Image sensor pixels 36 may be used collectively to form a light sensor (e.g., by binning sets of the pixels together or otherwise combining sensor pixel data) and/or may be arranged to gather light intensity data and position data (e.g., by forming an imager that is used form making location-dependent light intensity measurements). Processing unit 70 may be used to gather density (light-transmission) data, may be used to gather spectral data (e.g., by measuring sample transmittance under varying colors of illumination), may be used to gather fluorescence data (e.g., by measuring light that is emitted by the sample after light excitation from sources 78 and/or laser 72 or during light excitation from sources 78 and/or laser 72 using a color filter to block the excitation light from being detected by a light sensor), and may be used in making other measurements on cells 22. If desired, processing unit 70 may apply heat to cells 22 using heater 76 or may apply laser light from laser 72 to cells 22 (e.g., to destroy or otherwise affect undesired cells as part of a filtering scheme).

Figure 8:
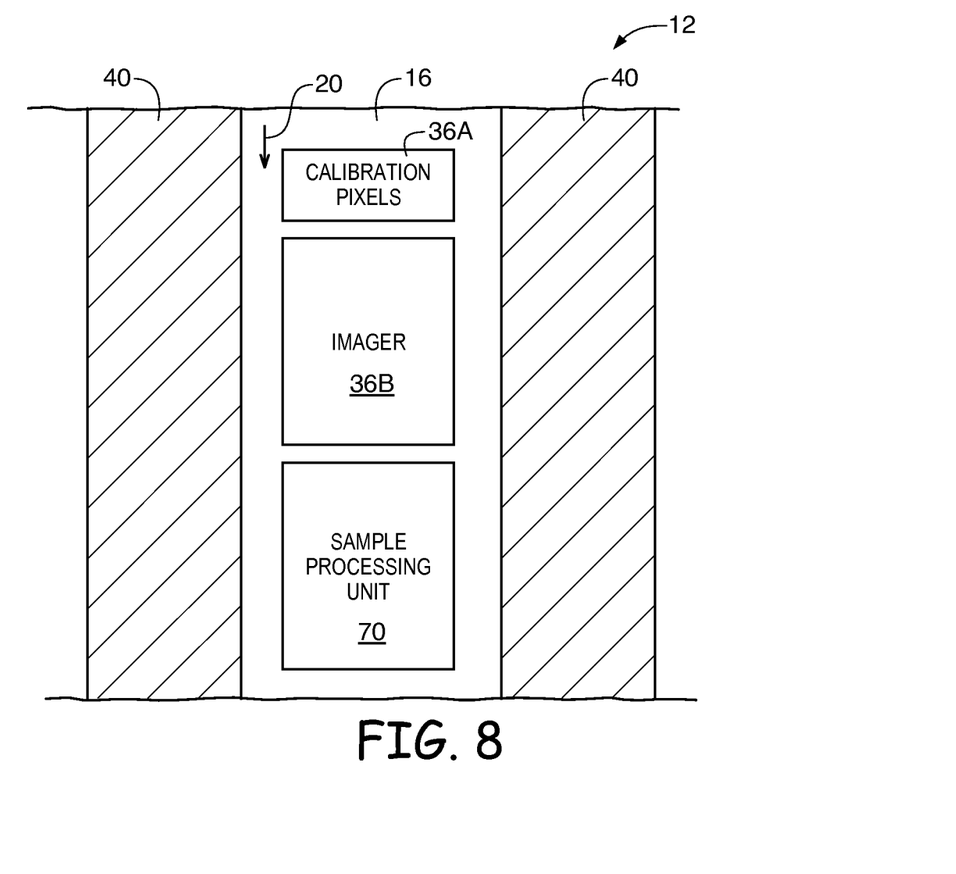
FIG. 8 is a top view of an illustrative fluid channel in a system of the type shown in FIG. 1 that has been provided with calibration pixels, imager pixels, and sample processing structures in accordance with an embodiment of the present invention.

A top view of an illustrative channel that has been provided with a sample processing unit such as sample processing unit 70 of FIG. 7 is shown in FIG. 8. As shown in FIG. 8, fluid 20 may flow past one or more calibration sensors such as calibration sensor 36A, one or more imagers such as imager 36B, and one or more sample processing units such as sample processing unit 70. The calibration sensors may be used to determine the flow rate and illumination level for cells 22 and may be used in making corresponding adjustments to flow rate, illumination intensity, and data acquisition rate (e.g., frame rate), as described in connection with FIG. 3. The imagers may be used in capturing images of cells 22 (or other samples). After determining the size and shape of the cells, the cells may flow past sample processing unit 70 for processing.

Figure 9:
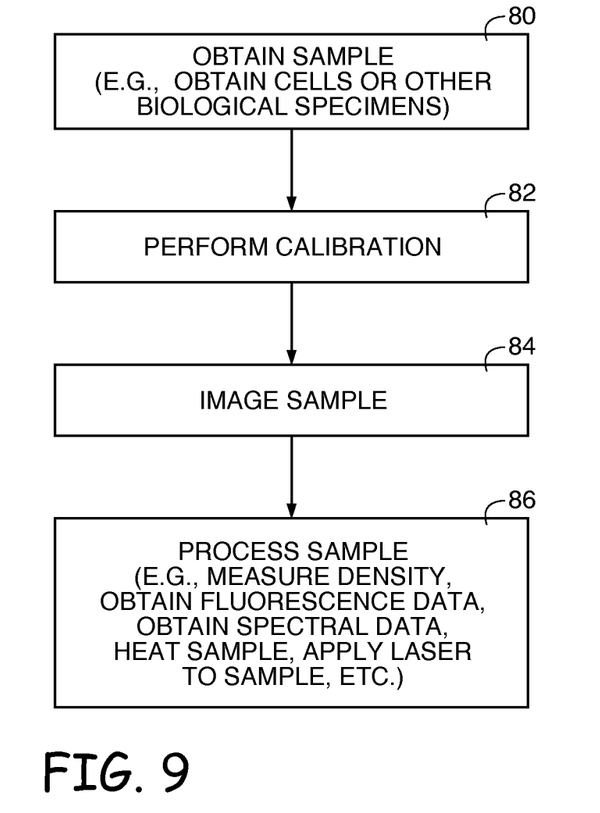
FIG. 9 is a flow chart of illustrative steps involved in using equipment of the type shown in FIG. 8 in imaging and processing cells or other samples in accordance with an embodiment of the present invention.

Illustrative steps involved in using a channel of the type shown in FIG. 8 in a system of the type shown in FIG. 1 to process cells, biological specimens, or other materials suspended in fluid are shown in FIG. 9.

At step 80, a user may obtain a cell sample or other biological sample. If desired, the sample may be mixed with a dilutant to produce a fluid of a desired viscosity for flowing through channel 16. The sample may be introduced into channel 16 via entrance port 24.

At step 82, the fluid of the sample may flow over calibration sensor 36A. Calibration operations may be performed using the image pixels in calibration sensor 36A. For example, the flow rate of the fluid may be measured, the amount of light being received by the image pixels in the calibration sensor may be used to determine that intensity of illumination 30, etc. Appropriate corresponding adjustments may be made to the imager associated with the calibration sensors.

During the operations of step 84, the fluid may flow over an imager. The image sensor pixels 36B in the imager may be used to capture image data for one or more cells or other particles in the fluid or other sample image data. The image data may be processed to produce images of the cell or other sample.

At step 86, the cells in the fluid or other sample may be processed using processing unit 70. The image data that was acquired during the operations of step 84 may be used during the processing operations of step 86. In particular, the image data may be correlated with fluorescence data obtained using sensors 36 during step 86, the image data may be used in locally targeting laser light from laser 72 to particular portions of a cell or other sample, the image data may be used in determining where and how much to heat the sample, where to illuminate the sample in connection with a fluorescence measurement, etc.

Figure 10:
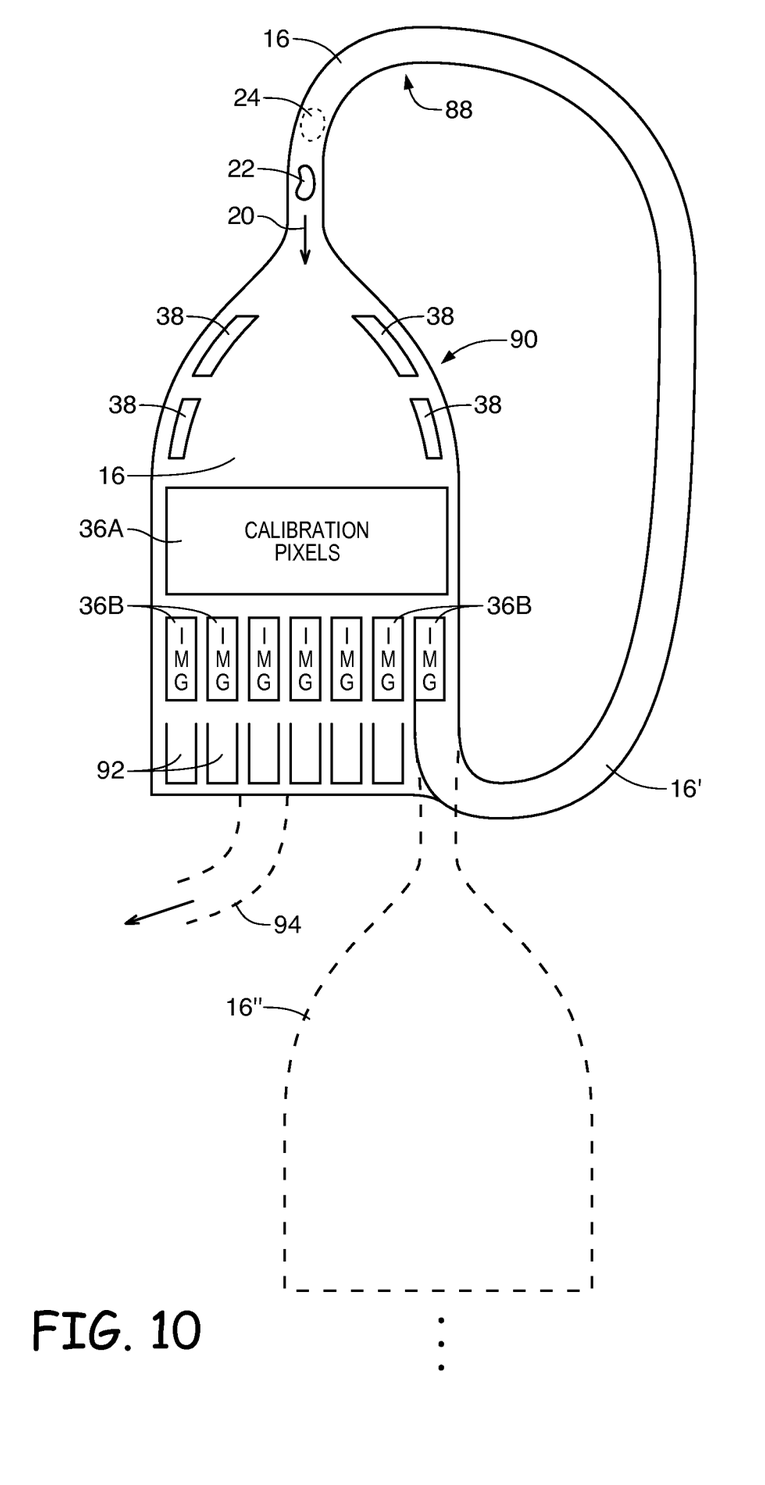
FIG. 10 is a diagram of optofluidic microscope fluid channels configured to serve as a liquid chromatograph in accordance with an embodiment of the present invention.

If desired, the sidewalls of channel 16 may be shaped to form a chromatograph (i.e., equipment for separating the cells or other particles in fluid 20 by weight and/or size or other particle characteristics). This type of arrangement is shown in FIG. 10. As shown in FIG. 10, channel 16 may have a first portion such as portion 88 in which channel 16 has a relatively constant width and may have a second portion such as portion 90 in which the channel width expands (e.g., by flaring outwards in a bell shape). Samples such as cells 22 in fluid 20 may be introduced into channel 16 via entrance port 24 and may flow through channel 16. Electrodes such as electrodes 38 may be used to propel fluid 20 (e.g., ionic fluid) through channel 16 or MEMs pumps or other structures may be used in controlling the flow of fluid 20. For example, electrodes 38 may be used in controlling the flow rate for fluid 20.

The expanded bell shape (flared shape) in portion 90 of channel 16 causes cells that are heavier and/or larger and that therefore travel more slowly to move towards the outer edges of channel 16 and causes cells that are lighter and/or smaller and that therefore travel more rapidly to move toward the center of channel 16.

Calibration sensor pixels 36A may be used to make flow rate measurements, illumination level measurements, and other calibration measurements for calibrating imagers 36B.

Imagers 36B may be used to capture images of the cells in fluid 20. Because heavier/larger cells are located near the outer edges of channel 16, the imagers that are located nearest the edges of channel 16 may be used to capture images of heavier and/or larger cells (or other particles in fluid 20) than the imagers that are located nearer the center of channel 16. Corresponding receptacles such as receptacles 92 may be used in collecting cells 22 following separation. The fluid in receptacles 92 may be retained for further study and processing or may be discarded. If desired, a discharge port such as discharge port 94 may be used to discard cells from a particular portion of the channel. For example, discard port 94 may be used to discard smaller and/or lighter cells from the center of channel 16. Channel portion 16' may, if desired, loop back to the entrance to flared portion 90 of channel 16 to allow for additional passes through portion 90. This allows cells 22 in fluid 20 to be separated with increased accuracy. There may be separate channels 16' on each side of flared portion 90. The arrangement of FIG. 10 in which only one side of flared portion 90 has been provided with a channel 16' is merely illustrative. One or more additional cascaded flared regions such as channel region 16" may also be provided (and may, if desired, be included in a loop that routes fluid 20 back to the entrance of region 90).

Various embodiments have been described illustrating apparatus for imaging and processing fluids containing cells and other materials. A sample may be introduced into a channel for imaging and processing. A calibration sensor may be used to determine the direction and flow rate associated with the fluid. The calibration sensor may also be used in measuring illumination levels. Using information such as the measured flow rate and illumination level, adjustments may be made to image acquisition pixels associated with an imager and flow rate control structures such as flow rate control electrodes. The imager may then be used to acquire images of the cells or other materials. A processing unit may include light sources that emit light of different colors, a laser, a heater, and image sensor pixels. The image sensor pixels in the processing unit, the calibration sensor, and the imager may be formed from pixels contained in a common image sensor integrated circuit. The processing unit may be used to gather transmission data, spectral data, fluorescence data, and other data on a sample. The processing unit may also use components such as the heater and laser to apply heat and/or light to the sample. For example, the processing unit may be used to selectively destroy cells that have certain attributes. A chromatograph may be formed using channels that have a bell-shaped expanding region. As fluid circulates through the bell-shaped region, cells or other particles move to the outside or inside of the channel depending on their weight and size. Imagers may be used to image cells or other particles that have been separated in this way.

The foregoing is merely illustrative of the principles of this invention which can be practiced in other embodiments.

What is claimed is:

1. Apparatus, comprising:
   an image sensor integrated circuit containing an array of image sensor pixels including calibration sensor pixels and imager sensor pixels;
   a fluid channel on the image sensor integrated circuit that is configured to receive fluid;
   a calibration sensor formed from the calibration sensor pixels; and
   an imager formed from the image sensor pixels.

2. The apparatus defined in claim 1 wherein the calibration sensor is configured to use the calibration sensor pixels to measure a flow rate for the fluid.

3. The apparatus defined in claim 2 wherein the calibration sensor is configured to use the calibration sensor pixels to measure light intensity.

4. The apparatus defined in claim 3 further comprising a light source that illuminates the channel, wherein the calibration sensor is configured to use the calibration sensor pixels to measure light intensity for light emitted by the light source.

5. The apparatus defined in claim 4 further comprising a transparent cover that covers that channel, wherein the light emitted by the light source passes through the transparent cover and wherein the channel has a longitudinal axis and a width perpendicular to the longitudinal axis that is less than 1 mm.

6. The apparatus defined in claim 5 wherein the fluid contains cells and wherein the imager is configured to acquire images of the cells.

7. The apparatus defined in claim 6 further comprising a processing unit in the channel that processes the cells.

8. The apparatus defined in claim 7 wherein the processing unit comprises a laser for destroying the cells after the imager acquires the images of the cells.

9. The apparatus defined in claim 7 wherein the processing unit comprises light sources of different colors.

10. The apparatus defined in claim 7 wherein the processing unit comprises a heater.

11. The apparatus defined in claim 1 wherein the fluid comprises cells and wherein the calibration unit is configured to use the calibration sensor pixels to measure the flow rate of the fluid and the cells and an illumination intensity in the channel, the apparatus further comprising a control circuit that adjusts the imager sensor pixels based at least partly on the measured flow rate and the measured illumination intensity.

* * * * *